United States Patent
Peterson et al.

(10) Patent No.: US 8,083,690 B2
(45) Date of Patent: Dec. 27, 2011

(54) CONVERTIBLE GUIDEWIRE SYSTEM AND METHODS

(75) Inventors: Dean Peterson, Rogers, MN (US); Jeff Welch, Maple Grove, MN (US); Howard Root, Excelsior, MN (US)

(73) Assignee: Vascular Solutions, Inc., Minneapolis, MN (US)

( * ) Notice: Subject to any disclaimer, the term of this patent is extended or adjusted under 35 U.S.C. 154(b) by 519 days.

(21) Appl. No.: 12/204,583

(22) Filed: Sep. 4, 2008

(65) Prior Publication Data

US 2010/0056955 A1    Mar. 4, 2010

(51) Int. Cl.
*A61B 5/00* (2006.01)
*A61M 25/00* (2006.01)

(52) U.S. Cl. ....................................................... 600/585
(58) Field of Classification Search .................. 600/585; 604/164.1, 164.05, 100.02, 528
See application file for complete search history.

(56) References Cited

U.S. PATENT DOCUMENTS

| | | | |
|---|---|---|---|
| 5,178,158 A | 1/1993 | de Toledo | |
| 6,537,295 B2 | 3/2003 | Petersen | |
| 2005/0090810 A1 | 4/2005 | Petersen et al. | |
| 2006/0217664 A1* | 9/2006 | Hattler et al. | 604/164.1 |
| 2007/0179472 A1* | 8/2007 | Whittaker et al. | 604/528 |
| 2009/0137870 A1* | 5/2009 | Bakos et al. | 600/116 |

* cited by examiner

*Primary Examiner* — Brian Szmal
(74) *Attorney, Agent, or Firm* — Patterson Thuente Christensen Pedersen, P.A.

(57) ABSTRACT

A guidewire converter for use in intravascular procedures along with a guidewire. The guidewire converter includes an elongate tubular structure defining a lumen having an inner diameter and a first outer diameter. The inner diameter of the lumen is sized to receive the guidewire for intravascular procedures. The guidewire converter includes a locking mechanism coupled to the elongate tubular structure that has a second outer diameter that is less than or substantially equal to the first outer diameter. Operation of the locking mechanism releasably secures the elongate tubular structure to the guidewire.

16 Claims, 4 Drawing Sheets

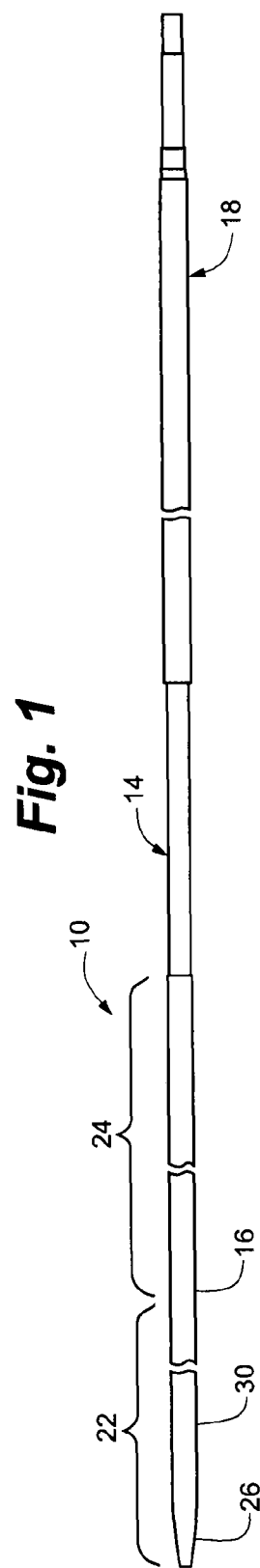

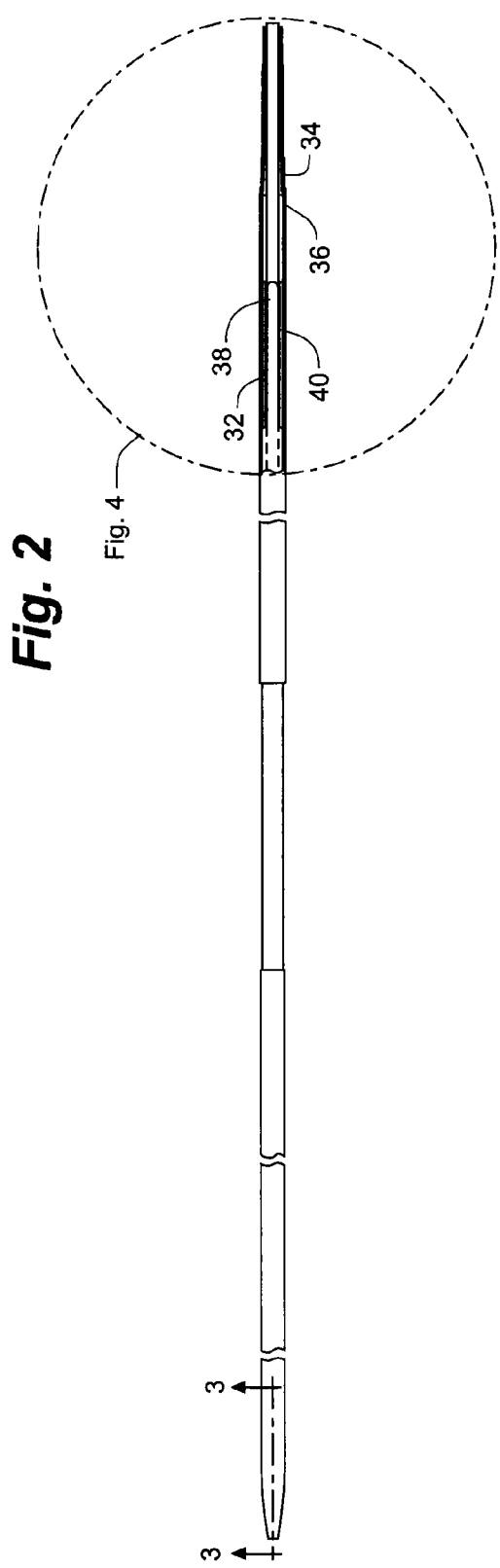

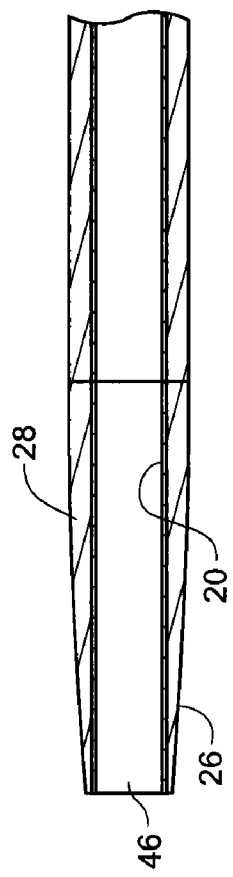

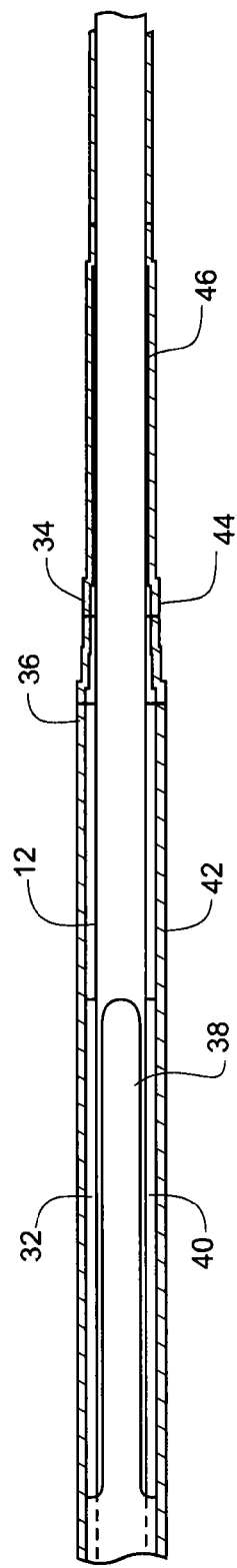

CONVERTIBLE GUIDEWIRE SYSTEM AND METHODS

FIELD OF THE INVENTION

The invention generally relates to guidewires that are used to guide medical instruments through the human vascular system. More particularly, the invention relates to the exchange of different guidewires having different qualities.

BACKGROUND OF THE INVENTION

Guidewires are commonly used in many medical procedures to assist a physician in gaining access to blood vessels within the body to insert instruments. For example, medical procedures involving accessing blood vessels in and around the heart often include making an incision in the femoral artery in the area of the groin or upper thigh, and inserting a medical guidewire into the femoral artery. A physician then manipulates the guidewire while observing it under fluoroscopy or by other imaging techniques to guide the guidewire to a desired location, for example, within the blood vessels in and around the heart.

Guidewires are available in a variety of sizes and configurations. For example, guidewires sizes include but are not limited to diameters of 0.014 inches and 0.035 inches. Guidewires are also available with a variety of tips in a variety of shapes and stiffnesses to accommodate the needs of physicians and to facilitate their manipulation of the guidewires through blood vessels.

Stylets and catheters are also used to access blood vessels in the human body to facilitate the introduction of intravascular leads, stents and other intravascular devices into the veins or arteries of the body. Although both stylets and guidewires are often thought of as simply very small wires, the purpose and operation of guidewires is significantly different as compared to stylets.

Intravascular procedures typically involve an initial step of introducing and routing a guidewire through a patient's vascular system to provide a rail or track along which additional intravascular devices may be introduced. Once a guidewire is in place, an introducer sheath catheter is routed over at least a portion of the guidewire to provide a larger opening into the vein or artery and sometimes to protect the inside walls of the vessels along the route of the guidewire. With the introducer in place, the guidewire may be removed or may remain in place as additional intravascular devices, such as intravascular leads, stents and catheters are introduced into the patient's vascular system.

To better accomplish the purpose of a guidewire providing a track along the patient's vascular system for other intravascular devices, it is desirable that the guidewire be extremely flexible and preferably have the ability to vary the flexibility of the distal tip and/or deflect the distal tip so as to aid in routing the guidewire through the patient's vascular system.

In contrast to the guidewire that serves as a track over which other intravascular devices are routed, a stylet is used within an internal lumen of an intravascular device both to push that device through the vascular system and to steer the device as it is being pushed. Although some intravascular devices are designed to steer themselves using internal core wires, almost all leads and some catheters have an inner channel or lumen into which a stylet may be inserted.

In addition to pushing the intravascular device through the vascular system by engaging the distal end of the device, the stylet also serves to deflect the distal end of the intravascular device so as to steer the distal end through the vascular system. Unlike the lead, catheter or guidewire, which is highly flexible and floppy, the stylet must be stiffer and more rigid so as to enable the stylet to push the lead or catheter through the patient's vascular system.

Conventionally, stylets having different bends on the distal end are used at different points of advancing the lead or catheter to a desired location. For straight segments of a vessel a straight stylet is used, whereas a stylet with a curved distal tip is used to navigate the lead or catheter through a curved portion of a vessel.

It is often necessary to change guidewire size during medical procedures. Currently, changing guidewire size involves withdrawing a guidewire that is currently located in the blood vessel and inserting a different size guidewire into the blood vessel and guiding it to the position previously occupied by the original guidewire. This can be a time consuming procedure, which lengthens the time necessary to a complete a medical vascular procedure and may increase discomfort and risk for the patient. In general, it is desirable to complete invasive medical procedures such as medical vascular procedures as quickly and efficient as possible to minimize stress on the patient.

Thus, there is room for improvement in the guidewire arts to improve efficiency and minimize time required to complete vascular medical procedures.

SUMMARY OF THE INVENTION

The present invention solves many of the above-referenced problems. A convertible guidewire of the present invention generally includes a guidewire and a guidewire converter.

The guidewire may be generally conventional and has a diameter smaller than the guidewire converter. The guidewire generally also has a length greater than that of a guidewire converter. For example, the guidewire may have an outside diameter of 0.014 inches while the guidewire converter has an outside diameter 0.035 inches. The guidewire converter covers a substantial portion of the length of the guidewire. For example, the guidewire converter may have a length of between about eighty and about one hundred forty five centimeters. Guidewires generally have a length of eighty to three hundred centimeters. These lengths should not be considered limiting.

Generally, in an example embodiment, the guidewire converter includes a distal sleeve portion and a locking portion. The distal sleeve portion may include a more rigid proximal portion and a less rigid portion that is distal to the more rigid distal portion. To ease the transition from the guidewire to the guidewire converter, the guidewire converter generally may include a tapered distal end. The tapered distal end may include a radiopaque marker band to facilitate visibility of the end of the guidewire converter to x-rays and fluoroscopy.

In an example embodiment, the lumen of the guidewire converter may be lined with a liner that covers the interior of the lumen. The liner may be formed of, for example, PTFE/polyimide or another polymer material. The more rigid portion of the guidewire converter may be formed from a polymer material, for example, nylon 12.

The less rigid portion of the guidewire converter may be formed from, for example Pebax having a Shore hardness of 55d, or another suitable biocompatible polymer.

In one embodiment, the distal sleeve portion of the guidewire converter may be externally coated with a hydrophilic coating.

Generally, the locking portion of the guidewire converter is constructed so as to have a maximum outer diameter that is no greater than the outer diameter of the distal sleeve portion 16.

In an example embodiment, if the distal sleeve portion has an outside diameter of 0.035 inches, then the locking portion should have a maximum outside diameter of 0.035 inches or less as well. These particular dimensions should not be considered to be limiting.

An example locking portion includes a locking sleeve and a collet. The locking sleeve is slidably movable over the collet and includes a tapered tube having a cylindrical portion and a tapered portion. The locking sleeve is slidably engageable to the collet so that when the fingers of the collet are within the cylindrical portion they are released from a guidewire that is inside the guidewire converter and so that when the locking sleeve is advanced so that the fingers of the collet are within the tapered portion they are frictionally squeeze down to engage a guidewire within the guidewire converter.

BRIEF DESCRIPTION OF THE DRAWINGS

FIG. 1 is a plan view of a guidewire converter in accordance with the present invention;

FIG. 2 is a partially plan view and partially cross sectional view of a guidewire converter in accordance with the present invention;

FIG. 3 is a cross-sectional view of a distal end of a guidewire converter in accordance with the present invention taken along section line 3-3 of FIG. 2; and FIG. 4 is a detailed cross-sectional view of an inner guidewire locking mechanism in accordance with the present invention taken from area 4 of FIG. 2.

DETAILED DESCRIPTION

Referring to FIGS. 1 and 2, convertible guidewire 10 of the present invention generally includes guidewire 12 and guidewire converter 14.

Guidewire 12 is a generally conventional guidewire of a diameter smaller than guidewire converter 14 and generally having a length greater than guidewire converter 14. Guidewire 12 may be any guidewire known to those skilled in the art as well as any sort of guidewire which may be developed following the filing of this application. For example, guidewire 12 may include a 0.014 inch diameter guidewire having a curved or straight end. Guidewire 12 may also include ends that are bent, J-shaped or any other end style known to those skilled in the art. Further, guidewire 12 may be a guidewire of any working diameter as long as it is smaller than guidewire converter 14 as will be seen.

In this example, guidewire converter 14 generally includes distal sleeve portion 16 and locking portion 18.

Referring to FIGS. 1, 2 and 3, an example embodiment includes liner 20, less rigid portion 22, more rigid portion 24 and tapered distal end 26. Distal sleeve portion 16 generally includes tapered distal end 26. Marker band 28 may be located proximate to tapered distal end 26. Marker band 28 may be formed of a radiopaque substance such as platinum iridium that is highly visible to x-ray imaging. Both more rigid portion 24 and less rigid portion 22 are flexible. However, less rigid portion 22 generally has greater flexibility that does more rigid portion 24.

Liner 20 may be formed of, for example, PTFE/polyimide. Liner 20 covers the interior of guidewire 12. More rigid portion 24 may be formed from a polymer material, for example, nylon 12. Less rigid portion 22 may be formed of, for example, Pebax having a Shore hardness of 55d. Less rigid portion 22 may extend, for example, for about 20 centimeters from taper distal end 26.

More rigid portion 24 generally extends from the end of less rigid portion 22 to locking portion 18. This length will be variable because guidewire converter 14 can be made in a variety of different lengths. For example, guidewire converter 14 may be made in overall lengths of 80 centimeters, 120 centimeters and 145 centimeters. These lengths are examples only and should not be considered to be limiting.

Distal sleeve portion 16 may be externally coated with hydrophilic coating 30. Hydrophilic coating 30 may extend for example, for about 40 centimeters proximally from tapered distal end 26.

In an example embodiment, intended for use in combination with a 0.014 inch diameter guidewire 12, guidewire converter 14 may have an outside diameter of 0.0350 inches and an inside diameter of 0.0175 inches.

Referring to FIGS. 1, 2 and 4, locking portion 18 has a maximum outside diameter no greater than the outside diameter of distal sleeve portion 16. For example, in an example embodiment, if distal sleeve portion 16 has an outside diameter of 0.0350 maximum then locking portion 18 has a maximum outside diameter of 0.0350 inches or less as well.

In an example embodiment, locking portion 18 includes collet 32, tapered tube 34 and inner locking sleeve 36. Collet 32 may, for example, include three fingers 38 formed by cutting three slots 40 into locking sleeve 36. Inner locking sleeve 36 has an outside diameter smaller than that of tapered tube 34 and distal sleeve portion 36. Locking sleeve 36 may be formed for example of 304 stainless steel, another biocompatible metal or a rigid polymer material.

Tapered tube 34, in an example embodiment, includes cylindrical portion 42 and tapered portion 44. Tapered tube 34 is dimensioned so that when collet 32 is moved into tapered portion 44 from cylindrical portion 42, collet 32 is forced radially inwardly to secure guide wire converter onto guidewire 12.

Guidewire converter 10 defines lumen 48. Lumen 48 is sized to receive guidewire 12.

The present invention also includes a method of providing a medical device including providing guidewire converter 14 along with instructions for its use. Providing the device includes sale directly on indirectly to a user, importing or exporting the device as well as giving the device to a user without payment. The providing of instructions includes providing instruction in writing or verbally as well as presentation of the instructions in a seminar in person, through a computer network or by telephone or video communication.

In operation when it is desired to convert a guidewire between two different sizes, a physician may make use of convertible guidewire 10 of the present invention. This description may refer to conversion between a 0.014 diameter guidewire and a 0.035 diameter guidewire, however, this is not intended to be limiting. Conversion may take place between any larger and smaller guidewire sizes in the context of the present invention.

For example, a physician may insert guidewire 12 inserted inside guidewire converter 14 into a blood vessel in the body. When it is desired to convert from the larger size guidewire to a smaller size guidewire, the physician may actuate locking portion 18 to release guidewire converter 14 from guidewire 12. Guidewire converter 10 is then removed over guidewire 12.

In one embodiment of the present invention, locking sleeve 36 is slid distally over collet 32 to release three fingers 38 from their grip on guidewire 12. Then guidewire 12 may be held in place while guidewire converter 14 is withdrawn over the top of guidewire 12.

Perhaps more commonly, a physician will wish to use convertible guidewire 10 to enlarge a smaller guidewire that has already been placed. In this circumstance guidewire 12 is pre-placed within a blood vessel. When it is desired to enlarge guidewire 12, convertible guidewire 10 is applied by placing the proximal end of guidewire 12 inside tapered distal end 26 of guidewire converter 14. Guidewire converter 14 is then advanced over guidewire 12 until the physician has positioned tapered distal end 26 of guidewire converter 14 at a desired location. The presence of marker band 28 facilitates the positioning of tapered distal end 26 by making tapered distal end 26 visible to fluoroscopy or ultra sound.

Once the physician has positioned guidewire converter 14 as desired, the physician may apply locking portion 18 to secure guidewire converter 14 to guidewire 12.

In order to do so, the physician grasps locking sleeve 36 and advances it toward the distal end of guidewire converter 14 a short distance. As locking sleeve 36 is advanced, three fingers 38 of collet 32 are comprised about guidewire 12 as three fingers 38 transition from cylindrical portion 42 to tapered portion 44 of tapered tube 34.

The invention may be embodied in other specific forms without departing from the spirit of the essential attributes thereof, therefore, the illustrated embodiments should be considered in all respects as illustrative and not restrictive, reference being made to the appended claims rather than to the forgoing description to indicate the scope of the invention.

The invention claimed is:

1. A convertible guidewire for use in guiding a medical device adapted to be insertable into a human vascular system, the medical device having structure for engaging the convertible guidewire, the convertible guidewire comprising:
   an inner guidewire having a first outer diameter, the inner guidewire having an extended length to reach from outside a body of a patient having the human vascular system to a desired medical device target delivery site inside the body, the inner guidewire being flexible to a greater degree near a distal end thereof than near a proximal end thereof, the inner guidewire being adapted to be maneuverable through a tortuous path within the vascular system to reach the desired medical device target delivery site;
   a guidewire converter comprising an elongate tubular structure having a length less than the extended length of the inner guidewire and defining a lumen having an inner diameter, the elongate tubular structure having a second outer diameter that is constant along most the length of guidewire converter and the second outer diameter being such that the structure for engaging is receivable over the second outer diameter to be routed to the desired medical target delivery site, the inner diameter of the lumen being such as to receive the inner guidewire therein for intravascular procedures and the second outer diameter being larger than the first outer diameter; and
   a locking mechanism operably coupled to the elongate tubular structure, the locking mechanism having a third outer diameter that is less than or equal to the second outer diameter wherein operation of the locking mechanism releasably secures the elongate tubular structure to the inner guidewire such that the convertible guidewire is convertible from a first size when the guidewire converter is secured to the inner guidewire to a second size when the inner guidewire is used alone such that the medical device can be passed over the proximal end of the inner guidewire or over the proximal end of the guidewire converter when the guidewire converter is secured to the inner guidewire by the locking mechanism.

2. The convertible guidewire as claimed in claim 1, the elongate tubular structure further comprising a distal less rigid portion and a proximal more rigid portion.

3. The convertible guidewire as claimed in claim 1, further comprising a tapered distal end including a radiopaque marker proximate the distal end.

4. The convertible guidewire as claimed in claim 1, wherein the locking mechanism further comprises a collet and a locking sleeve, the locking sleeve being slidably movable relative to the collet such that the collet is releasably securable to the inner guidewire.

5. A guidewire converter for use in intravascular procedures along with a guidewire having an extended length, comprising:
   an elongate tubular structure defining a lumen, the elongate tubular structure having a length less than the extended length, an inner diameter and a first outer diameter, the first outer diameter being constant along most of the length and the first outer diameter being sized to accommodate other intravascular medical devices routed over the guidewire converter to a desired medical target delivery site, the inner diameter of the lumen being such as to receive the guidewire for intravascular procedures; and
   a locking mechanism operably coupled to the elongate tubular structure, the locking mechanism having a second outer diameter that is less than or equal to the first outer diameter such that operation of the locking mechanism releasably secures the elongate tubular structure to the guidewire wherein operation of the locking mechanism releasably secures the elongate tubular structure to the inner guidewire such that the medical device can be passed over the proximal end of the inner guidewire or over the proximal end of the guidewire converter when the guidewire converter is secured to the inner guidewire by the locking mechanism.

6. The guidewire converter as claimed in claim 5, the elongate tubular structure further comprising a distal less rigid portion and a proximal more rigid portion.

7. The guidewire converter as claimed in claim 5, further comprising a tapered distal end including a radiopaque marker proximate the distal end.

8. The guidewire converter as claimed in claim 5, the locking mechanism further comprising a collet and a locking sleeve, the locking sleeve being slidably movable relative to the collet such that the collet is releasably securable to the inner guidewire.

9. A method of providing a medical device, comprising:
   providing a guidewire converter comprising an elongate tubular structure defining a lumen having an inner diameter, the elongate tubular structure having a first outer diameter the first outer diameter being constant along most of a length of the elongate tubular structure, the inner diameter of the lumen being such as to receive an inner guidewire for intravascular procedures and the guidewire converter further comprising a locking mechanism operably coupled to the elongate tubular structure, the locking mechanism having a second outer diameter that is less than or equal to the first outer diameter wherein operation of the locking mechanism releasably secures the elongate tubular structure to the inner guidewire; and
   providing instructions to:
   insert the inner guidewire into a blood vessel;
   pass the guidewire converter over the inner guidewire;

releasably lock the guidewire converter to the inner guidewire; and pass a medical device into the blood vessel to a desired medical target delivery site with at least a portion of the medical device passing over the guidewire converter and into the blood vessel.

10. The method as claimed in claim 9, wherein the elongate tubular structure further comprises a distal less rigid portion and a proximal more rigid portion.

11. The method as claimed in claim 9, wherein the guidewire converter further comprises a tapered distal end including a radiopaque marker proximate the distal end.

12. The method as claimed in claim 9, wherein the locking mechanism further comprises a collet and a locking sleeve, the locking sleeve being slidably movable relative to the collet such that the collet is releasably securable to the inner guidewire.

13. A method of providing a medical device, comprising:
providing a guidewire converter comprising an elongate tubular structure defining a lumen having an inner diameter, the elongate tubular structure having a first outer diameter, the first outer diameter being constant along a length of the elongate tubular structure and the first outer diameter being sized to accommodate other intravascular medical devices routed over the guidewire converter to a desired medical target delivery site, the inner diameter of the lumen being such as to receive an inner guidewire for intravascular procedures;

a locking mechanism operably coupled to the elongate tubular structure, the locking mechanism having a second outer diameter that is less than or equal to the first outer diameter wherein operation of the locking mechanism releasably secures the elongate tubular structure to the inner guidewire; and providing instructions to:
insert the inner guidewire with the guidewire converter releasably secured thereover into a blood vessel;
advance the inner guidewire with the guidewire converter releasably secured thereover until a distal end of the inner guidewire is at a desired location;
release the guidewire converter from the inner guidewire; and
withdraw the guidewire converter from the blood vessel over the inner guidewire.

14. The method as claimed in claim 13, wherein the elongate tubular structure further comprises a distal less rigid portion and a proximal more rigid portion.

15. The method as claimed in claim 13, wherein the guidewire converter further comprises a tapered distal end including a radiopaque marker proximate the distal end.

16. The method as claimed in claim 13, wherein the locking mechanism further comprises a collet and a locking sleeve, the locking sleeve being slidably movable relative to the collet such that the collet is releasably securable to the inner guidewire.

* * * * *